United States Patent
Frost et al.

(10) Patent No.: US 7,544,334 B2
(45) Date of Patent: Jun. 9, 2009

(54) DEVICE FOR STERILIZING OBJECTS

(75) Inventors: Robert Frost, Landshut (DE); Gernot Keil, Munich (DE); Peter G. Scheubert, Munich (DE); Peter Awakowicz, Munich (DE)

(73) Assignee: Ruediger Haaga GmbH, Donzdorf (DE)

( * ) Notice: Subject to any disclaimer, the term of this patent is extended or adjusted under 35 U.S.C. 154(b) by 863 days.

(21) Appl. No.: 10/506,788

(22) PCT Filed: Feb. 28, 2003

(86) PCT No.: PCT/EP03/02068

§ 371 (c)(1),
(2), (4) Date: Mar. 15, 2005

(87) PCT Pub. No.: WO03/075965

PCT Pub. Date: Sep. 18, 2003

(65) Prior Publication Data

US 2005/0168153 A1 Aug. 4, 2005

(30) Foreign Application Priority Data

Mar. 8, 2002 (DE) .................... 102 10 898

(51) Int. Cl.
*B01J 19/08* (2006.01)
(52) U.S. Cl. ...................................... 422/186
(58) Field of Classification Search ............... 422/186
See application file for complete search history.

(56) References Cited

U.S. PATENT DOCUMENTS 5,309,063 A 5/1994 Singh
5,669,975 A 9/1997 Ashitani

FOREIGN PATENT DOCUMENTS

| EP | 1 126 504 A | 8/2001 |
| GB | 2 066 076 A | 7/1986 |
| WO | WO 90 11784 A | 10/1990 |

*Primary Examiner*—Kishor Mayekar
(74) *Attorney, Agent, or Firm*—Crowell & Moring LLP

(57) ABSTRACT

An arrangement for sterilizing objects by using a low-pressure plasma. The arrangement includes an evacuable chamber for holding the objects, which evacuable chamber can be connected to a conduit for gas to be ionized. A high frequency transmitting device with an antenna system is provided for inductive generating of an alternating current plasma in the chamber. The antenna system includes two plasma generating coils spaced apart from each another.

11 Claims, 2 Drawing Sheets

DEVICE FOR STERILIZING OBJECTS

BACKGROUND AND SUMMARY OF THE INVENTION

This application claims the priority of German Patent Document No. 102 10 898.6, filed 8 Mar. 2002, and PCT/EP03/02068, filed 28 Feb. 2003 the disclosure of which is expressly incorporated by reference herein, respectively.

The present invention relates to an arrangement for sterilizing objects by a low-pressure plasma, including an evacuable chamber for taking up the objects, which evacuable chamber can be connected to a conduit for gas to be ionized, and including a high frequency transmitting device with an antenna system for inductive generating of an alternating current plasma in the chamber.

The sterilizing effect of a plasma lies in a mechanical destruction of microorganisms by a ion bombardment, and further in a chemical destruction by occuring radicals as well as destruction by ultraviolet light. Using a minimum of energy, the plasma can penetrate into the smallest surface cracks and holes, whereby with increasing low pressure, the temperature can be reduced to such an extent that even heat-sensitive objects, for example medical implants containing plastic, can be processed.

There are several possibilities for generating the high frequency power in the chamber, of which, when a particularly high electron density is required, the inductive plasma generating method has proven to be favourable. Antenna systems for inductive generating of an alternating current plasma usually include a ring antenna in the form of a plasma generating coil, whereby an alternating magnetic field positioned perpendicularly on the coil surface, induces an electrical field, which generates, in the gas to be ionized, a electrodeless ring discharge similar to a transformer secondary winding.

Known arrangements using inductive generation of an alternating current plasma in the area of a bordering wall in a chamber have the disadvantage whereby, with increasing distance to the plasma generating coil in the chamber, a strongly inhomogeneous distribution of the electron density is generated, so that objects in close proximity to the high-frequency plasma generating coils are plasma-treated more intensively than those at a distance further away.

It is an object of the present invention to improve the homogeneity of the electron density distribution in the chamber in order that the objects to be sterilized are more evenly treated by the low pressure plasma, in particular in the instance of larger, three-dimensional extension of the objects.

This object has been achieved in accordance with the present invention in that the antenna system includes two plasma generating coils set at a distance apart from one another.

In contrast to known chambers, which, for the purposes of sterilizing objects by low-pressure plasma, use only one plasma generating coil for inductive generating of an alternating current plasma, the arrangement according to the present invention results in a significantly more even electron density distribution. When a given, defined distance is provided between the two plasma generating coils, the electron density distribution of the two plasma generating coils superimpose and accumulate the distribution so that in a larger space between said coils, an electron density is achieved which is, substantially constant. This is particularly true when the distance between the plasma generating coils corresponds approximately to the diameters of the coils. This distance should ideally exceed the extension of the objects to be sterilized. This can be achieved by location of the plasma generating coils in the area of two bordering walls of the chamber, which walls are disposed opposite one another.

The design of the plasma generating coils themselves is irrelevant. Planar or spiral-shaped plasma generating coils can be used advantageously on the bordering walls of the chamber. A possible alternative is to wind helix-shaped plasma generating coils in the area of the bordering walls of the chamber around the chamber.

According to the alternating current plasma of the present invention, large-volume objects can be sterilized, whereby the achievable reduction in microorganisms per time interval on the overall surface is at least approximately the same. The arrangement according to the present invention is therefore particularly advantageous for medical purposes, for example for the sterilizing of implants and bone replacement material as well as medical devices such as sets of instruments, endoscopes or syringes.

In addition to relatively short sterilization times, which, according to the material of the objects, lie in the range of between several tens of seconds and approximately 20 minutes, further positive side effects arise from the arrangement according to the present invention:

In the case of hip implants, which are usually composed of a material combination of titan or ceramic for the ball and ultrahigh molecular polyethylene for the socket, an intended surface modification of the polyethylene can be achieved in that the wear behaviour of the surface is purposely reduced. The thickness of the modified layer is hereby controllable by the reaction time of the plasma.

BRIEF DESCRIPTION OF THE DRAWINGS

These and further objects, features and advantages of the present invention will become more readily apparent from the following detailed description thereof when taken in conjunction with the accompanying drawings wherein.

DETAILED DESCRIPTION OF THE DRAWINGS

Figure 1:
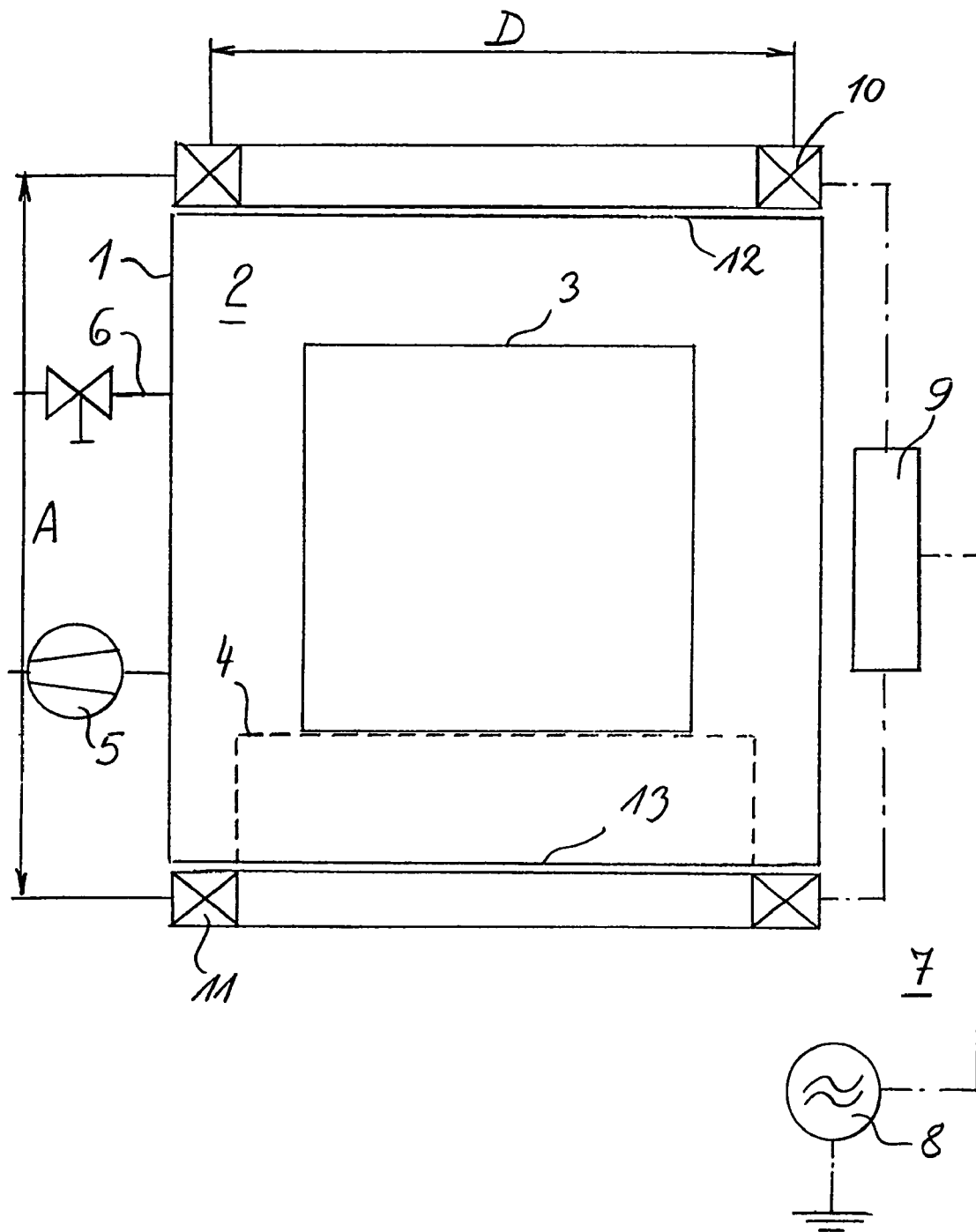
FIG. 1 is an arrangement according to the present invention for sterilizing objects by means of a low-pressure plasma.

The arrangement according to FIG. 1 includes a reactor housing 1 having a chamber 2 which sterilizes by using a low pressure plasma. This chamber 2 can take up objects 3 to be sterilized, which are placed on a holding device 4 denoted by a broken line. The chamber 2 is connected to a vacuum pump system 5 as well as to a conduit 6 for gas to be ionized. Further necessary additional devices, which are not essential to the present invention, are not shown here.

A high-frequency transmitting device 7 generates an alternating current plasma in the chamber 2. The high-frequency transmitting device 7 has a high-frequency generator 8. Via an adapter network 9, also known as a matchbox, the high-frequency generator 8 is connected to an antenna system, which, in accordance with the present invention, includes two plasma generating coils 10 and 11 set at a distance to one another. Between the plasma generating coils 10 and 11, which have a middle diameter D, there is a distance A, which should, if possible, exceed the extension of the objects 3 to be sterilized. The plasma generating coils 10 and 11 are therefore applied for the purposes of the present invention in the area of two opposing border walls 12 and 13 of the reactor housing 1.

The vacuum pump system 5 can advantageously include a plurality of pumps which serve to evacuate the chamber 2, and consist, for example, of a combination of a Roots pump and a slide vane rotary pump, by means of which the chamber 2 can be evacuated to a low pressure of approximately 1 Pa. The high-frequency generator 8 functions preferably at a permissible radio frequence of 13.56 MHz, in the case of a regulated power consumption of up to 5 kW. The adapter network 9 serves the reflexion-free generating of the high-frequency energy in the plasma.

The plasma generating coils 10 and 11 are applied, for the purposes of inductive generating of the alternating current plasma, outside of the chamber 2. The plasma generating coils 10 and 11 are connected with the high-frequency voltage, which causes a magnetic alternating field of the excitation frequency in axial direction in the inside of the plasma generating coils 10 and 11. This magnetic field in turn induces an electric rotational field, whose field lines wind in a ring shape around the magnetic field lines.

The evacuable reactor housing 1 must be made of dielectrical material, as otherwise wall currents could prevent the alternating field from entering the chamber 2.

The improved electron density distribution according to the present invention is described below with the aid of FIG. 2.

Figure 2:
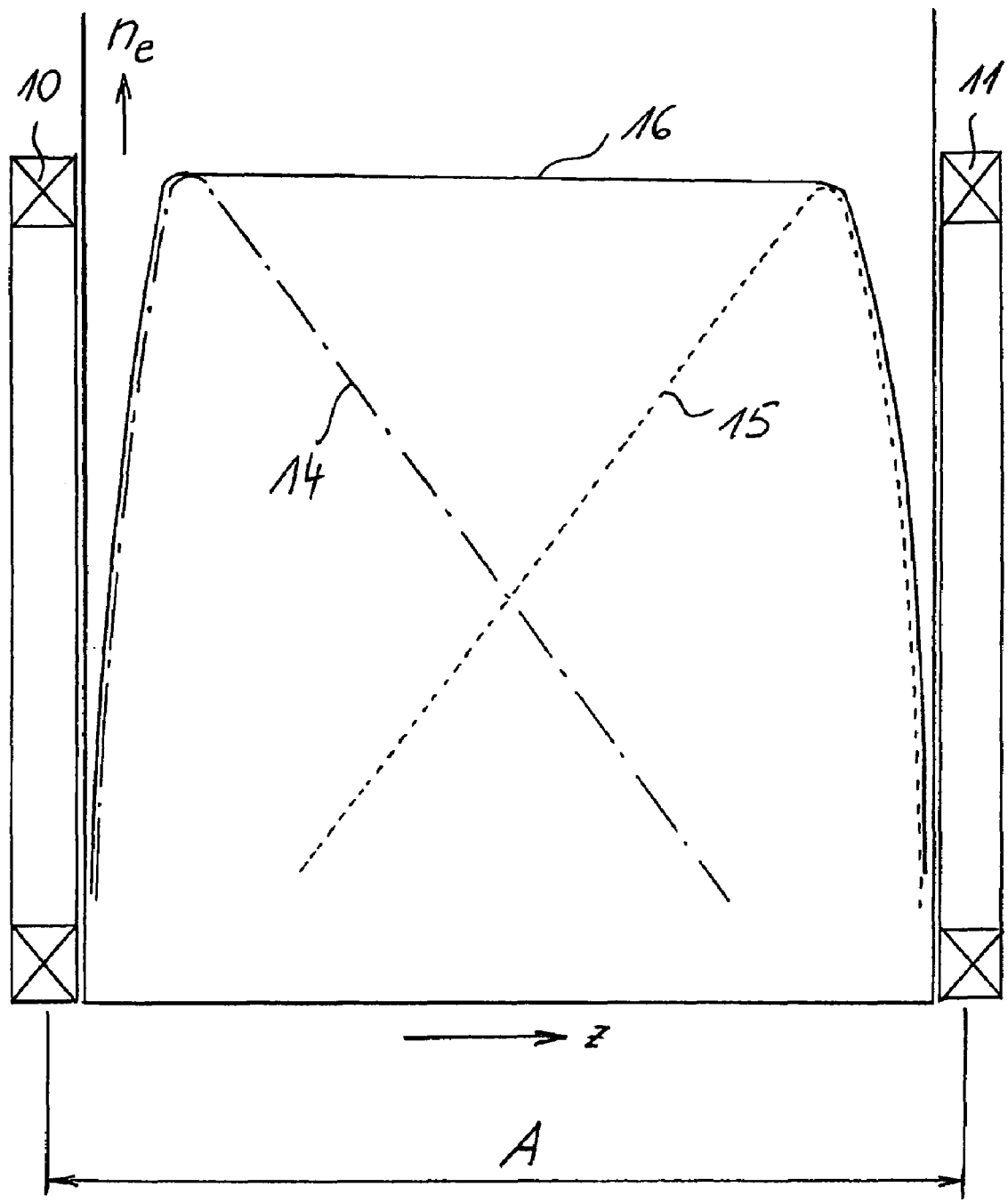
FIG. 2 is a graphical representation to demonstrate the improved electron density distribution in the chamber according to the present invention.

In the graphical representation in FIG. 2, the ordinate ne shows the electron density distribution and the absciss z shows the height of the chamber 2. The plasma generating coils 10 and 11 can be seen at a distance A to one another.

If only one plasma generating coil 10 were present, as is the case in standard arrangements, then an electron density distribution according to the dot-dash curve 14 would arise in the chamber 2. If, on the other hand, only the plasma generating coil 11 were present, then an electron density distribution according to the dotted curve 15 would arise in the chamber 2.

Because two plasma generating coils 10 and 11 are present at an appropriate distance A to one another, the electron density distributions of the two curves 14 and 15 are superimposed on one another. This is shown schematically by the unbroken line 16, which is to be understood as a cumulative curve, which represents the true electron density distribution in the chamber 2 in the presence of two plasma generating coils 10 and 11. It can be seen that the curve 16 has a longer, horizontal branch, whose length, correspond to the extension of the object 3 to be sterilized. In such a case, the ideal electron density distribution for sterilizing the object 3 arises.

The invention claimed is:

1. Apparatus for sterilizing objects by low-pressure plasma, said apparatus comprising:
    an evacuable chamber for retaining said objects, a gas conduit for delivering gas to be ionized to said evacuable chamber; and
    a high frequency transmitting device including an antenna system for inductive generation of an alternative current plasma in said evacuable chamber, said antenna system comprising two plasma generating coils spread apart from each other,
    wherein a distance between the plasma generating coils corresponds to an average diameter of said coils.

2. The apparatus according to claim 1, wherein the plasma generating coils are located in the area of two opposing border walls of the evacuable chamber.

3. The apparatus according to claim 2, wherein a distance between the plasma generating coils exceeds an extension of the objects to be sterilized.

4. The apparatus according to claim 2, wherein both plasma generating coils are connected to a common high-frequency generator.

5. The apparatus according to claim 1, wherein a distance between the plasma generating coils exceeds an extension of the objects to be sterilized.

6. The apparatus according to claim 5, wherein both plasma generating coils are connected to a common high-frequency generator.

7. The apparatus according to claim 1, wherein both plasma generating coils are connected to a common high-frequency generator.

8. A sterilizer comprising:
    an evacuable chamber; and two plasma generating coils spread apart by a predetermined distance and configured to inductively generate an alternating current plasma,
    wherein the predetermined distance between the plasma generating coils corresponds to an average diameter of said coils.

9. The apparatus according to claim 8, wherein the plasma generating coils are located in the area of two opposing border walls of the evacuable chamber.

10. The apparatus according to claims 8, wherein the predetermined distance between the plasma generating coils exceeds an extension of the objects to be sterilized.

11. The apparatus according to claims 8, wherein both plasma generating coils are connected to a common high-frequency generator.

* * * * *